US009255051B2

(12) United States Patent
Gaffney et al.

(10) Patent No.: US 9,255,051 B2
(45) Date of Patent: Feb. 9, 2016

(54) EFFICIENCY, FLEXIBILITY, AND PRODUCT VALUE OF A DIRECT ALKANES TO OXYGENATES PROCESS

(71) Applicant: Gas Technologies LLC, Walloon Lake, MI (US)

(72) Inventors: Ian Lawrence Gaffney, Los Gatos, CA (US); Evan Michael Visser, Hull, IA (US); Walter Breidenstein, Boyne Falls, MI (US)

(73) Assignee: Gas Technologies LLC, Walloon Lake, MI (US)

( * ) Notice: Subject to any disclaimer, the term of this patent is extended or adjusted under 35 U.S.C. 154(b) by 259 days.

(21) Appl. No.: 13/844,217

(22) Filed: Mar. 15, 2013

(65) Prior Publication Data

US 2014/0275642 A1 Sep. 18, 2014

(51) Int. Cl.
*C07C 29/50* (2006.01)
*C07C 27/00* (2006.01)
*C07C 41/09* (2006.01)
*C01B 3/26* (2006.01)

(52) U.S. Cl.
CPC . *C07C 29/50* (2013.01); *C01B 3/26* (2013.01); *C07C 41/09* (2013.01); *C01B 2203/0277* (2013.01)

(58) Field of Classification Search
CPC ........................................................ C07C 27/00
USPC ........................................................ 518/700
See application file for complete search history.

(56) References Cited

U.S. PATENT DOCUMENTS

| | | | |
|---|---|---|---|
| 2,130,080 A | 9/1938 | Evans | |
| 2,376,668 A | 5/1945 | Derby et al. | |
| 2,977,386 A | 3/1961 | Kise et al. | |
| 3,282,983 A | 11/1966 | Lachowicz et al. | |
| 4,065,421 A | 12/1977 | Allyn et al. | |
| 4,276,055 A | 6/1981 | Huang | |
| 4,417,903 A | 11/1983 | Hinkamp | |
| 4,541,835 A | 9/1985 | Norton et al. | |
| 4,541,837 A | 9/1985 | Norton et al. | |
| 4,603,662 A | 8/1986 | Norton et al. | |
| 4,618,451 A | 10/1986 | Gent | |
| 4,760,210 A | 7/1988 | Sweeney | |
| 4,833,171 A | 5/1989 | Sweeney | |
| 5,628,805 A | 5/1997 | Lif et al. | |
| 6,013,114 A | 1/2000 | Hille et al. | |
| 6,255,357 B1 | 7/2001 | Abbott | |
| 6,270,541 B1 | 8/2001 | Basu et al. | |
| 6,486,362 B1 | 11/2002 | Forestiere et al. | |
| 6,514,299 B1 | 2/2003 | Bean et al. | |
| 6,548,681 B1 | 4/2003 | Chopade et al. | |
| 6,599,336 B2 | 7/2003 | Hamada | |
| 6,846,951 B1 | 1/2005 | Thiebaut | |
| 7,005,529 B2 | 2/2006 | Eek-Vancells | |
| 7,456,327 B2 | 11/2008 | Pawlak et al. | |
| 7,470,811 B2 | 12/2008 | Thiebaut | |
| 7,578,981 B2 | 8/2009 | Pawlak et al. | |
| 7,615,085 B2 | 11/2009 | Schwab et al. | |
| 7,642,293 B2 | 1/2010 | Pawlak et al. | |
| 7,687,669 B2 | 3/2010 | Pawlak et al. | |
| 7,846,978 B2 | 12/2010 | Olah et al. | |
| 7,879,296 B2 | 2/2011 | Pawlak et al. | |
| 7,910,787 B2 | 3/2011 | Pawlak et al. | |
| 8,148,589 B2 | 4/2012 | Gracey et al. | |
| 8,193,254 B2 | 6/2012 | Pawlak et al. | |
| 8,202,916 B2 | 6/2012 | Pawlak et al. | |
| 8,293,186 B2 | 10/2012 | Pawlak et al. | |
| 8,410,183 B2 | 4/2013 | Cortright et al. | |
| 2002/0026744 A1 | 3/2002 | Golubkov et al. | |
| 2006/0223892 A1 | 10/2006 | Pawlak et al. | |
| 2007/0100005 A1 | 5/2007 | Pawlak et al. | |
| 2007/0130822 A1 | 6/2007 | Araya | |
| 2009/0069607 A1 | 3/2009 | Smith, Jr. et al. | |
| 2010/0041776 A1 | 2/2010 | Czernichowski et al. | |
| 2010/0158760 A1 | 6/2010 | Pawlak et al. | |
| 2010/0242347 A1 | 9/2010 | Eberhard | |
| 2011/0040129 A1 | 2/2011 | Loescher | |
| 2012/0142973 A1 | 6/2012 | Su et al. | |

(Continued)

FOREIGN PATENT DOCUMENTS

EP 0 0407 038 B1 1/1995
WO 2008-135801 A2 11/2008

OTHER PUBLICATIONS

International Search Report mailed Jan. 8, 2015 in PCT/US2014/058628, filed Jan. 1, 2015, 4 pgs.
Nunan, J.G. et al., "Methanol and 2-Methyl-1-Propanol (Isobutanol) Coupling to Ethers and Dehydration over Nafion H: Selectivity, Kinetics, and Mechanism," J. of Catalysis 139, pp. 406-420 (1993).
Zhang, X. et al., "Synthesis of methylal by catalytic distillation," Chemical Engineering Research and Design 89, pp. 573-580 (2011).
International Search Report mailed Aug. 22, 2014 for PCT/US2014/030161, Filed Mar. 17, 2014, 4 pgs.

(Continued)

*Primary Examiner* — Elvis O Price
(74) *Attorney, Agent, or Firm* — Brooks Kushman P.C.

(57) ABSTRACT

A method for preparing oxygenated hydrocarbons includes steps of: reacting a first heated hydrocarbon-containing gas stream with an oxygen-containing gas stream in a reactor for form a first product blend, recovering the energy generated in the reactor in order to preheat incoming hydrocarbon feed to the reactor and/or to drive endothermic reactions that generate synthesis gas, separating and condensing one or more liquid oxygenated hydrocarbons from the product stream, separating a reject stream from a recycle stream, mixing remaining gaseous hydrocarbon product from the recycle stream with the first hydrocarbon-containing gas stream after one reaction cycle, converting the first reject stream to a synthesis gas mixture, and converting the synthesis gas mixture to light alkanes to be blended with one or with oxygenates in an output stream to optionally form higher molecular weight oxygenates.

25 Claims, 1 Drawing Sheet

(56) References Cited

U.S. PATENT DOCUMENTS

| | | |
|---|---|---|
| 2012/0232311 A1 | 9/2012 | Hsieh et al. |
| 2013/0035519 A1 | 2/2013 | Lee et al. |
| 2014/0475642 | 9/2014 | Gaffney et al. |

OTHER PUBLICATIONS

International Search Report mailed Jul. 2, 2014 in PCT/US2014/027256, filed Mar. 14, 2014, 6 pgs.

International Search Report mailed Jul. 29, 2014 in PCT/US2014/028368, filed Mar. 14, 2014, 4 pgs.

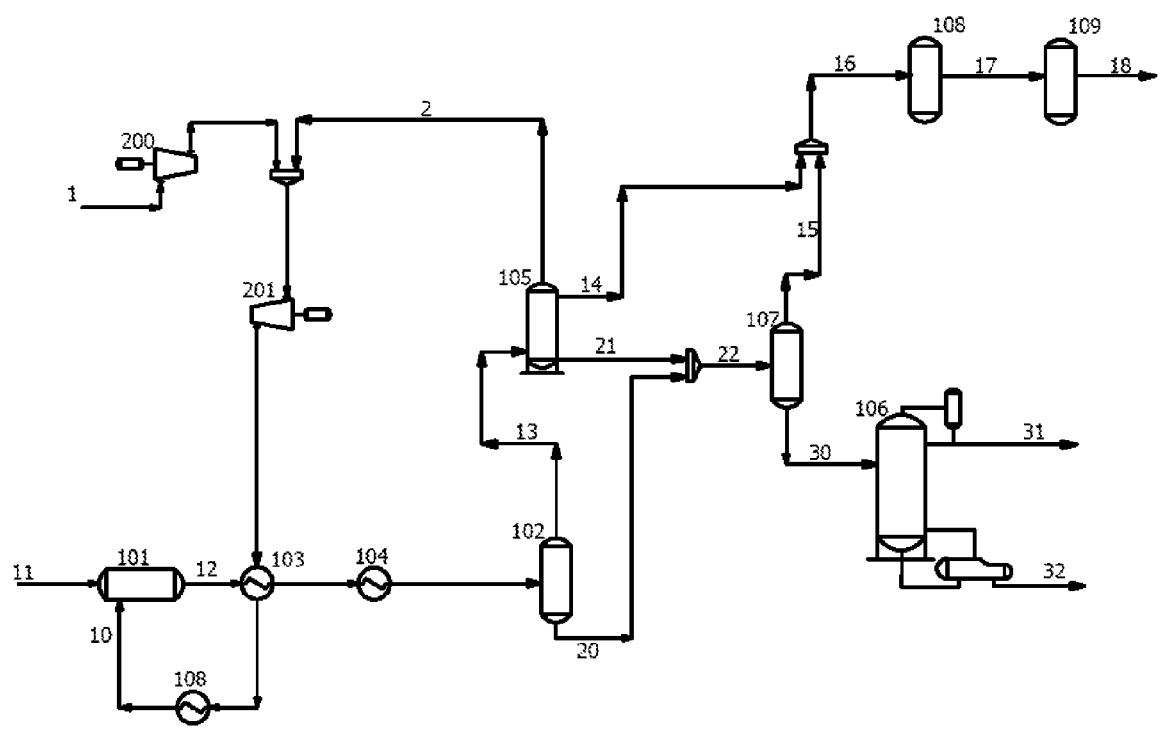

EFFICIENCY, FLEXIBILITY, AND PRODUCT VALUE OF A DIRECT ALKANES TO OXYGENATES PROCESS

TECHNICAL FIELD

In at least one aspect, the present invention relates to methods and equipment for partially oxidizing a hydrocarbon feed gas.

BACKGROUND

Steam reforming of natural gas is currently the most cost effective method of producing hydrogen and carbon oxides. The gaseous mixture of hydrogen and carbon oxides (carbon monoxide and/or carbon dioxide) is hereinafter referred to as "synthetic gas" or "syngas". Syngas is useful as an intermediate for the manufacture of products such as ammonia, methanol or synthetic petroleum. Currently, commercial methanol production is almost entirely based on reforming light hydrocarbons, especially methane, first to syngas, followed by syngas clean up, methanol synthesis, and methanol separation. This process has been the dominant route of methanol production since the 1920's. The entire process, however, is cumbersome with a high degree of complexity and associated costs. Therefore, a direct method has been developed using direct homogenous partial oxidation of methane to methanol (the "DHPO" method).

The DHPO method is however generally limited by the need to choose between high conversions and high selectivity to obtain economic yields of methanol. In both catalytic and non-catalytic DHPO methods, higher conversions tend to create the co-products hydrogen, carbon oxides, and water, whereas higher selectivity leads to lower conversion rates which has traditionally made the process uneconomic.

U.S. Pat. Nos. 8,293,186; 8,202,916; 8,193,254; 7,910,787; 7,687,669; 7,642,293; 7,879,296; 7,456,327; and 7,578,981 overcome some of the known DHPO system limitations by using a reactor quench step and a high volume recycle system with integrated separations and low pressure drop. These patents describe these DHPO system improvements in detail and are incorporated herein by reference. However, despite the improved efficiency of our DHPO process, relative and comparable to that of the syngas-based methanol synthesis, carbon oxides and hydrogen are produced in our DHPO system process. This can limit the overall carbon efficiency to less than 100%. Furthermore, to limit the buildup of such gases and nitrogen, the process requires a reject gas stream such as a purge. Said reject gas often contains some alkane content, lowering carbon efficiency.

Furthermore, the DHPO process reactor as described in our aforementioned patents and patent applications is unable to process synthesis gas. Because of this, the process excludes a wide range of carbonaceous materials from being advantageously utilized.

Accordingly, there is a need for methods and apparatuses that can produce synthesis gas from the reject gasses from the recycle loop as well as utilize synthesis gas produced gas from a variety of carbonaceous materials for enhanced carbon efficiency and process yields, as well as that can utilize the waste heat generated by the exothermic DHPO reaction

SUMMARY

The present invention solves one or more problems of the prior art by providing in at least one aspect a method and apparatus for more efficiently synthesizing oxygenated hydrocarbons, e.g. methanol, ethanol, formaldehyde, acetaldehyde, etc. The present embodiment combines the benefits of a direct homogeneous partial oxidation (DHPO) system and the flexibility of synthesis gas such as to increase the molecular carbon content of the DHPO product and utilize the waste heat of the DHPO process. In our improved DHPO system, synthesis gas already created by over-oxidation inherent with the DHPO reactor, the alkane content of the reject gasses, and heat surplus recoverable from direct partial oxidation, are utilized to enhance the carbon efficiency of the overall process as well as create chemicals of an increased molecular carbon content which traditionally have higher value than the components of the original oxygenated products. Furthermore, the reject streams which are used to create synthesis gas cannot be accepted as feed by the DHPO reactor yet are more fully scrubbed of impurities such as sulfur that are known to poison catalysts which transform synthesis gas into oxygenates or feed alkanes.

In the present invention, these materials and energy streams of the former DHPO systems which formerly been wasted in the prior art are used herein to provide a DHPO system which more efficiently and cost-effectively produces oxygenated hydrocarbons. This novel ability to more fully utilize the carbon content of the gasses rejected by the recycle loop eliminates the traditionally mutually exclusive choice between reactor conversion and selectivity in regards to overall process yield. In addition, the use of higher nitrogen content in feed oxygen traditionally necessitated higher purge rates and lower carbon efficiency. The present invention allows for the usage of higher nitrogen content in the feed oxygen for lowered capital costs again without the sacrifice of overall process yield.

In an embodiment, a method for preparing oxygenated hydrocarbons includes steps of:

a) reacting a first heated hydrocarbon-containing gas stream with an oxygen-containing gas stream in a reactor forming a first product blend, b) recovering the energy generated in the reactor in order to preheat incoming hydrocarbon feed to the reactor and/or to drive endothermic reactions that generate synthesis gas, c) separating and condensing one or more liquid oxygenated hydrocarbons from the product stream;

d) separating a reject stream from a recycle stream, e) mixing remaining gaseous hydrocarbon products from the recycle stream with the first hydrocarbon-containing gas stream after one reaction cycle;

f) converting the first reject stream to a synthesis gas mixture; and g) converting the synthesis gas mixture to light alkanes to be blended with the DHPO feed gas or with oxygenates in an output stream to optionally form higher molecular weight oxygenates.

BRIEF DESCRIPTION OF THE DRAWINGS

FIG. 1 is a schematic illustration of a system for removing formaldehyde from a partially oxidized hydrocarbon.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "synthetic gas" or "syngas" as used herein refers to gaseous mixture of hydrogen and/or carbon oxides (carbon monoxide and/or carbon dioxide).

With reference to FIG. 1, a schematic illustration of an apparatus a process for converting a carbonaceous gas to oxidized products in a gas-to-chemicals (GTL) process is provided. In a refinement, the apparatus functions in a continuous manner when in operation. Homogeneous direct partial oxidation is performed in a reactor 101 which is supplied with a hydrocarbon-containing gas 10 and an oxygen-containing gas 11. In a refinement, the reaction is operated at pressures from about 450 to 1250 psia and temperatures from about 350 to 450° C. In particular, hydrocarbon-containing gas 10 and an oxygen-containing gas 11 react in a vessel to form a first product blend which is a blend (i.e., a mixture) of partially oxygenated compounds that include formaldehyde. In a refinement, the first product blend and/or output streams 31, 32 include $C_{1-10}$ alcohols and/or $C_{1-5}$ aldehydes. In another refinement, the first product blend and/or output streams 31, 32 include an alcohol selected from the group consisting of methanol, ethanol, propanols, butanols, pentanols and combinations thereof, and/or aldehyde selected from the group consisting formaldehyde, acetaldehyde, propionaldehyde and combinations thereof. In another refinement, the first product blend and/or output streams 31, 32 include an alcohol selected from the group consisting of methanol, ethanol, and combinations thereof, and aldehyde selected from the group consisting formaldehyde, acetaldehyde, and combinations thereof. Examples of systems and methods of performing the partial oxidation as set forth in U.S. Pat. Nos. 8,293,186; 8,202,916; 8,193,254; 7,910,787; 7,687,669; 7,642,293; 7,879,296; 7,456,327; and 7,578,981; the entire disclosures of which are hereby incorporated by reference. In a refinement, the hydrocarbon-containing gas includes $C_{1-10}$ alkanes. In another refinement, the hydrocarbon-containing gas includes an alkane selected from the group consisting of methane, ethane, propanes, butanes, pentanes and combinations thereof. In another refinement, the hydrocarbon-containing gas includes an alkane selected from the group consisting of methane, ethane, and combinations thereof. Examples of oxygen containing gas include molecular oxygen which may be in the form of concentrated oxygen or air. In a refinement, the oxygen-containing gas stream is made oxygen rich (e.g., by passing air through a membrane to increase oxygen content). The low conversion and selectivity of homogeneous direct partial oxidation requires that a recycle loop is utilized to increase the overall carbon efficiency.

Following partial oxidation reaction the reactant stream is rapidly cooled in a series of heat exchangers 103 and 104 to prevent decomposition of the produced oxygenates. The heat energy transferred by exchanger 104 might optionally be used to provide energy which may be used in the creation of synthesis gas. After cooling the liquids are separated from the gas stream as station 102. The gas stream is then submitted to a separation process for removal of non-hydrocarbon fractions a station 105 which may be performed via scrubbing, membrane separation, adsorption processes, cryogenic separations, or by purging a small gas fraction. If station 105 is a liquid scrubbing system, liquid products are sent to a flash drum 107 where dissolved gases are removed. Non-hydrocarbon gases 14 are removed from the recycle loop, and the hydrocarbon gases 2 are then recycled to combine with fresh methane gas 1 which has been pressurized to the pressure of the loop by compressor 200. The stream composed of recycled hydrocarbons plus fresh methane gas is pressurized to make up for pressure losses in the recycle loop, preheated via the cross exchanger 103 and further by the preheater 108, when necessary, to meet the desired reaction conditions.

Liquids generated by the gas-to-chemicals process are composed predominantly of alcohols and aldehydes (e.g., methanol, ethanol and formaldehyde) as set forth above. The raw liquid stream 22 generated by the GTL process is generally composed of 50-70% alcohols and 5-20% aldehydes 15-30% water. Downstream processing of these liquids may include a number of different synthesis routes to higher-value chemicals and fuels, but simple distillation of alcohols from aldehydes is performed in a simple fractional distillation column 106 in which alcohols are recovered in the distillate 31 and the aqueous aldehyde solution from the column bottoms 32.

The compositions of the streams 14 obtained from separation of non-hydrocarbon gases from the recycle loop and from degassing the liquid mixture 15 may vary significantly depending on the separation methods employed in station 105. Stream 15 would be typically be needed to regenerate a scrubbing fluid by liberating dissolved gasses such as carbon dioxide or carbon monoxide, which would be enriched in this stream. Stream 15 is composed predominantly of lighter hydrocarbons and carbon oxides (e.g., $CO_2$ and/or) which are soluble in the liquid solution, but are vaporized when decreasing the pressure.

Stream 15 may or may not be blended with stream 14 depending on the needs of the synthesis gas reactor 108. Stream 14 is a separated gas stream form station 105 such might be separated from a purge stream, membrane, cryogenic, or adsorption process. Although stream 14 would be enriched in non-hydrocarbon gasses, there would be some light alkanes present as well. A simple purge method in station 105 results in hydrocarbon fractions that may reach up to 70%, while selective removal techniques tend to preserve hydrocarbons in the recycle loop 2. Stream 14 and 15 are blended to form stream 16, which is rich in synthesis gas.

Stream 16 goes through a reactor 108, which converts the hydrocarbon portion to synthesis gas in stream 17. Stream 17 then goes on to react with liquid streams in reactor 109 (for example output streams 31 or 32). Stream 32 is the bottoms product of distillation column 106 and would contain low volatility, high boiling components such as formalin, heavy alcohols, and some acids. Stream 31 is the overhead from distillation column 106 and would be rich in the higher volatility low boiling components such as light alcohols. Streams 17 and said liquid product streams would then react to form oxygenates of a carbon number greater than that in the liquid reactant stream. Such oxygenates produced by reactor 109 might include esters such as formates and DMC, or carboxylic acids from a CO rich synthesis gas in stream 17. Higher alcohols and aldehydes from mixed alcohol synthesis, alcohol homologation, and aldehyde synthesis can form from a relatively hydrogen rich synthesis gas in stream 17. As mentioned, stream 32 contains aqueous formaldehyde, which is known to react with synthesis gas to form glycolic acid and glycol aldehyde. In another refinement, the synthetic gas is generated by a pyrolysis reaction or generated externally and blended with stream 17. In a further refinement, the pyrolysis reaction generates light alkanes in addition to synthetic gas.

Alternatively, stream 17 may react with itself in reactor 109 and form light alkanes (e.g., $C_{1-4}$ alkanes) for use as a feed gas to be blended with stream 1. The light alkane product of this reaction would typically be rich in $C_2+$ hydrocarbons, which are known to produce a distribution of alcohols with a higher molecular weight when compared to methane under homogenous partial oxidation conditions. Certain catalysts are also known to produce both alcohols and light alkanes. In addition, stream 17 may be blended with externally produced synthesis gas to produce a gas mixture in reactor 109 which can be utilized by reactor 101. This feature allows for feedstock flexibility in the direct homogenous partial oxidation process. In another variation, the synthesis gas is generated in a reactor 108 by implementing a steam, dry, or tri-reforming reaction. In a refinement, the tri-reforming reaction is assisted by energy (e.g., it uses the heat) recovered from a heat exchanger 104

In one embodiment, DHPO gas rejected by a DHPO recycle loop is used to produce syngas in reactor 108. The syngas further reacts to produce both oxygenates and light alkanes in reactor 109. The conversion may be effected using a suitable catalyst, for example, an actinide/lanthanide modified catalyst as described in U.S. Pat. No. 4,762,588. DHPO Oxygenate products may be separated from light alkanes using any simple liquid separation system well-known in the art. The separated alkanes may then be blended with the feed gas in stream 1 following nitrogen removal, if necessary.

In another embodiment, in a DHPO system comprising a synthesis gas, the gas may be separated in the recycle system using one or more membranes alkanes such as might be found with station 105. Many membrane materials lack sufficient selectivity to completely separate non-hydrocarbon such as nitrogen and carbon dioxide from hydrocarbon streams. In this configuration, the light alkanes can be present in the permeate or retentate streams of the membrane. Using well known techniques, this stream would be converted into synthesis gas. Hydrogen and carbon dioxide may optionally be separated from this synthesis gas in stream 17 by a membrane or scrubbing system prior to reactor 109 to make a stream rich in CO which could then be used in carbonylation and carbon insertion reactions in reactor 109. The hydrogen may optionally be used further reduce the carbonylated species. Alternatively, syngas is known to react directly with alcohols and form higher alcohols, esters, or aldehydes.

In another embodiment, some of the light alkanes present in stream 16 may be thermally decomposed to provide hydrogen and carbon black in reactor 108. This thermal decomposition may be assisted by heat exchanger 104. The carbon black could either be partially combusted in oxygen to yield pure carbon monoxide or reacted with the carbon dioxide to yield carbon monoxide. This pure carbon monoxide can then be used as a reactant in carbonylation or carbon insertion reactions in reactor 109. The hydrogen may optionally be used further reduce the carbonylated species present in stream 18 after reactor 109.

Further to the previous embodiment, an external carbon source may be utilized to react with carbon dioxide to yield carbon monoxide in either a catalytic or non-catalytic process assisted by heat recovered by heat exchanger 104. The carbon monoxide may then be reacted with oxygenates in carbon insertion or carbonylation reactions in a manner consistent with the previous embodiment.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for preparing oxygenated hydrocarbons, comprising:
    a) reacting a first heated hydrocarbon-containing gas stream with an oxygen-containing gas stream in a reactor to form a first product stream;
    b) recovering energy generated in the reactor in order to preheat incoming hydrocarbon feed to the reactor and/or to drive endothermic reactions that generate synthesis gas,
    c) separating and condensing one or more liquid oxygenated hydrocarbons from the first product stream;
    d) separating a reject gas stream and a recycle gas stream from the first product stream;
    e) mixing remaining gaseous hydrocarbon product from the recycle stream the recycle gas stream with the first heated hydrocarbon-containing gas stream after one reaction cycle;
    f) converting the reject gas stream to a synthesis gas mixture; and
    g) converting the synthesis gas mixture to light alkanes to be blended with the first heated hydrocarbon-containing gas stream or with oxygenates in an output stream to form higher molecular weight oxygenates.

2. The method of claim 1 further comprising separating the synthesis gas by a liquid scrubbing system, absorption, purge stream, membrane separations, or cryogenic separations.

3. The method of claim 1 wherein the oxygen-containing gas stream is made oxygen rich.

4. The method of claim 3 wherein the oxygen-containing gas stream is made oxygen rich by passing air through a membrane to increase oxygen content.

5. The method of claim 1 wherein synthesis gas is separately generated and then blended with the output stream produced in step g).

6. The method of claim 5 wherein the synthesis gas that is separately generated is heated by energy from steps a) and b) through a heat exchanger.

7. The method of claim 5 wherein the synthesis gas that is separately generated is injected into a recycle system in order to scrub undesired components and re-separate non-hydrocarbon components after step d).

8. The method of claim 1 wherein synthesis gas is contacted with a catalyst.

9. The method according to claim 1 wherein the synthesis gas is generated externally to be blended with synthesis gas mixture of step f) or in a reactor for implementing a steam, dry, or tri-reforming reaction.

10. The method according to claim 1 wherein a tri-reforming reaction is heated by energy recovered from a heat exchanger.

11. The method according to claim 1 wherein carbon oxides but not hydrogen is separated with a scrubbing system and/or a membrane.

12. The method according to claim 1 wherein hydrogen and/or CO are reacted directly with oxygenates in a liquid output stream.

13. The method according to claim 1 wherein carbon dioxide generated internally and recovered or supplied externally is reacted with carbon, producing an enriched carbon monoxide gas in a process heated by energy recovered from steps a) and b).

14. The method according to claim 1 wherein alkane conversion to synthesis gas occurs in the presence of a catalyst.

15. The method according to claim 1 wherein the synthesis gas is generated internally or externally by a pyrolysis reaction heated by energy recovered from steps a) and b).

16. The method according to claim 13 where a pyrolysis reaction generates light alkanes in addition to synthesis gas.

17. The method according to claim 1 wherein a reactor generates synthesis gas with a membrane reactor.

18. The method according to claim 1 wherein the synthesis gas self-reacts to form $C_{1-4}$ alkanes.

19. The method of claim 1 wherein the first heated hydrocarbon-containing gas stream includes $C_{1-10}$ alkanes.

20. The method of claim 1 wherein the first heated hydrocarbon-containing gas stream includes an alkane selected from the group consisting of methane, ethane, propanes, butanes, pentanes and combinations thereof.

21. The method of claim 1 wherein the first heated hydrocarbon-containing gas stream includes an alkane selected from the group consisting of methane, ethane, and combinations thereof.

22. The method of claim 1 wherein the output streams includes $C_{1-10}$ alcohols.

23. The method of claim 1 wherein output streams includes an alcohol selected from the group consisting of methanol, ethanol, propanols, butanols, pentanols and combinations thereof.

24. The method of claim 1 wherein the first product stream includes an alcohol selected from the group consisting of methanol, ethanol, and combinations thereof.

25. The method according to claim 1 where the first product stream to be reacted with synthesis gas is produced from reactive distillation and includes dialkyl ethers.

* * * * *